US006447988B2

(12) United States Patent
Lynch et al.

(10) Patent No.: US 6,447,988 B2
(45) Date of Patent: *Sep. 10, 2002

(54) IN VITRO ASSAY METHOD FOR THE STUDY OF BRAIN AGING

(75) Inventors: Gary S. Lynch; Eric Bednarski, both of Irvine; Charles E. Ribak, Laguna Miguel; Christine M. Gall, Irvine, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/787,784

(22) Filed: Jan. 22, 1997

(51) Int. Cl.[7] .................................................. C12Q 1/00
(52) U.S. Cl. ............................. 435/4; 435/368; 435/375
(58) Field of Search ........................ 435/4, 40.5, 40.52, 435/325, 363, 366, 368

(56) References Cited

PUBLICATIONS

Bahr, BA et al. Induction of β–amyloid–containing polypeptides in hippocampus: Evidence for a concomitant loss of synaptic proteins and interactions with an excitotoxin. *Exp. Neurol.* (1994) 129:81–94.

Bahr, B.A. Mini–review: long–term hippocampal slices: a model system for investigating synaptic mechanisms and pathologic processes. *J. Neurosci. Res.* (1995) 42:294–305.

Bahr, B.A., et al., "Spectrin breakdown products increase with age in telenephalon of mouse brain," *Neurosci Lett.* (1991) 131:237–40.

Bednarski, E. and Lynch, G. "Cytosolic proteolysis of catepsin D in hippocampus following suppession of cathpsins B and L," *J. Neurochemistry* (1996) 67:1846–55.

Braak, H., "Spindle–shaped appendages of IIIab–pyramid filled with lipofuscin: A striking pathological change of the senescent human isocortex", *Acta Neuropathol.* (1979) 46:197–202.

Brizze, K.R. et al., "The amount and distribution of pigments in neurons and glia of the cerebral cortex." *J. Geront.* (1969) 24:127–35.

Brunk, U.T. et al. "A novel hypothesis of Lipothesis of lipofuscinogenesis and cellular aging based on interactions between oxidative stress and autophagocytosis," *Mutation Res.* (1992) 275:395–403.

Brunk, U. and Ericsson, J.L.E.,"Electron Mircroscopical studies on rat brain neurons. Localization of acid phosphatase and mode of formation of lipofuscin bodies," *J. Ultrastuct. Res.* (1972) 38:1–15.

Chatterjee, S. and Nolder, M. "An aggregate brain cell culture model for studying neuronal degeneration and regeneration" *J. Neural Transm. Suppl.* (1994) 44:47–60.

Dowson, J.H. et al. "Changes in intraneuronal lipopigment in Alzheimer's disease", *Neurobiol. Aging* (1992) 13:493–500.

Dunn, WA Jr, et al., "Growth factor–induced neurite growth in primary neuronal cultures of dogs with neuronal ceroid lipofuscinosis." *Int. J. Dev. Neurosci.* (1994) 12(3):185–96.

Fletcher, B.L., "Measurement of fluorescent lipid peroxidation products in biological systems and tissues," *Analyt. Biochem.* (1973) 52:1–9.

Gahwiler, B.H. "Organotypic cultures of neural tissue." *Trends Neurosci.* (1988) 11:484–9.

Glees, P., and Hansan, M. "Lipofuscin in neuronal aging and diseases." *Normal Pathol. Anat.* (1976) 32:1–68.

Harman, D. "Lipofuscin and ceroid formation: the cellular recycling system." in Porta, E.A., ed. *Lipofuscin and ceroid pigments.* New York: Plenum Press; 1990:3–15.

Mann, D.M.A. et al., "The relationship between lipofuscin pigment and ageing in the human nervou system." *J. Neurol. Sci.* (1978) 37:83–93.

Roy, D. et al. "Effects of chlorpromazine on the activities of antioxidant enzymes and lipid peroxidation in the various regions of aging rat brain." *J. Neurochemistry* (1984) 42:628–33.

Sohal, R.S. and Wolfe, L.S., "Lipofuscin: Characteristics and significance." In: *Progress in Brain Research*, Swaab et al. (eds), Elsevier Science Publishers, 1986, vol. 70, pp. 171–183.

Stoppini et al. "A simple method for organotypic cultures of nervous tissue" *J. Neurosci. Meth.* (1991) 37:173–182.

Tappel, A. et al., "Effect of antioxidants and nutrients on Lipid peroxidation fluorescent products and aging Parameters in the Mouse." *J. Gerontol.* (1973) 28(4):415–24.

Terry, R. "Interrelations among the lesions of normal and abnormal aging of the brain." In: *Progress in Brain Research*, (eds), Elsevier Science Publications, 1986, vol. 70, pp. 41–47.

Terry et al., "Ultrastructural studies in Alzheimer's presenile dementia." Am. J. Pathol. (1964) 44:269–97.

*Primary Examiner*—Laurie Scheiner
*Assistant Examiner*—J. S. Parkin
(74) *Attorney, Agent, or Firm*—Karl Bozicevic; Paula A. Borden; Bozicevic, Field & Francis, LLP

(57) ABSTRACT

Cultured brain slices are treated with a free radical generator, in the presence of a lysosomal enzyme inhibitor (specifically an inhibitor of two cathepsins). The treated brain slices rapidly develop autofluorescent lipofuscin granules—a universal feature of brain aging. Other correlates of the aged brain are also induced by this treatment, thereby providing an in vitro model for (1) the study of brain aging; (2) assessment of anti-brain aging drugs; and (3) therapeutics directed at the clinical condition referred to as neuronal ceroidlipofuscinosis.

16 Claims, No Drawings

IN VITRO ASSAY METHOD FOR THE STUDY OF BRAIN AGING

STATEMENT AS TO FEDERALLY SPONSORED RESEARCH

Material described herein was developed, at least in part, with funds from NIA via Grant AG00538 and AFOSR via Grant 95-I-0304 and the government may have certain rights in this material.

FIELD OF THE INVENTION

This invention relates generally to the field of biological assays and more particularly to an in vitro model for brain aging and neuronal ceroid-lipofuscinosis.

BACKGROUND OF THE INVENTION

Aging in neuronal tissue is characterized by a variety of features, including: (1) high concentrations of β-amyloid in plaque-like structures, (2) high concentrations of ceroid-lipofuscin, a lysosomal pigment that contains lipoidal moieties and emits yellow to greenish autofluorescence under ultraviolet illumination (Brizzee K. R. et al., "The amount and distribution of pigments in neurons and glia of the cerebral cortex." J. Geront. (1969) 24:127–35; Sohal, R. S. and Wolfe, L. S., "Lipofuscin: Chararacteristics and significance." In: *Progress in Brain Research*, Swaab et al. (eds), Elsevier Science Publications, 1986, Vol. 70, pp. 171–183.), (3) loss of synaptic proteins, such as synaptophysin, (4) neurofibrillary tangles, (5) abnormal phosphorylation of neurotubule proteins, (6) neuronal atrophy (Bahr, BA et al., "Induction of β-amyloid containing polypeptides in hippocampus:evidence for a concomitant loss of synaptic proteins and interactions with an excitotoxin", Exp. Neurol. (1994) 129:81–94.), (7) lipofuscin-filled somatic expansions, known as meganeurites, (Braak, H., "Spindle-shaped appendages of IIIab-pyramidals filled with lipofuscin: A striking pathological change of the senescent human isocortex", Acta Neuropathol. (1979) 46:197–202.), (8) an increase in the number of perikaryal lysosomes (Brunk, U. and Ericsson, J. L. E. "Electron microscopical studies on rat brain neurons. Localization of acid phosphatase and mode of formation of lipofuscin bodies", J. Ultrastr. Res. 38 (1972) 38:1–15; Cataldo, A. M. et al., "Properties of the endosomal-lysosomal system in the human central nervous system: Disturbances mark most neurons in populations at risk to degeneration in Alzheimer's disease", J. Neurosci. (1996) 16:186–99), (9) fragmentation of cytoskeletal proteins (Bahr, B. A., et al., "Spectrin breakdown products increase with age in the telencephalon in mouse brain", Neurosci. Lett. (1991) 131:237–40), (10) a degeneration of myelinated axons (Peters, A., et al., "The effects of aging on area 46 of the frontal cortex of the rhesus monkey", Cerebral Cortex (1994) 4:621–35), and (11) cellular processes (neurites) filled with dense lysosomal bodies and vacuoles (Terry et al., "Ultrastructural studies in Alzheimer's presenile dementia." Am. J. Pathol. (1964) 44: 269–297.) These characteristics, including the production of lipofuscin, are apparent in Alzheimer's disease.

Lipofuscin accumulation is also present in a condition known as neuronal ceroid lipofuscinosis (NCL). NCL is a storage disease that generally becomes evident in early adult life, although it can also occur later in adult life or during childhood. Usually the disease begins with mental deterioration, followed by seizures and ataxia, amongst other symptoms. Central nervous system deterioration with cerebral atrophy is found, and biopsy of the brain reveals the presence of lipofuscin granules. Electron microscopy reveals abnormal inclusions witophin lysosomes in a wide variety of tissues, such as the fibroblast and endothelial cells of the conjunctiva and skin. It is uncertain whether this disorder is a true lysosomal storage disease; single or multiple genetic disorders may be present (Beaudet, A. L. Lysosomal Storage Diseases. In: Harrison's Principles of Internal Medicine, 12th Edition. Wilson, J. D. et al.(eds) McGraw-Hill, Inc. New York, (1991), pg.1854.)

The lack of knowledge about aging and NCL is due in part to the lack of an in vitro model. A genetic model of NCL does exist. Recently, Dunn and his colleagues (Dunn, W A Jr, Raizada, M. K., Vogt, E S, and Brown, E. A. Growth factor-induced neurite growth in primary neuronal cultures of dogs with neuronal ceroid lipofuscinosis. Int. J. Dev. Neurosci. (1994) 12(3): 185–96) established conditions to grow neuronal cells from newborn English setters with NCL. The characteristic inclusion bodies were present in the neurons, and a time-dependent maturation of the inclusion bodies was noted.

Research on the processes underlying brain aging is made difficult by (1) the time span over which the processes act, (2) the complexity of the neural and glial networks involved, (3) the intricate relationships between the wide variety of biochemical and structural changes that occur with aging, and (4) the relative inaccessibility of the brain to prolonged experimental manipulation. The hippocampus is a region of the brain involved in memory encoding and has been shown to exhibit early degeneration in Alzheimer's disease and ischemia, thus it is an excellent area to use in the study of aging (Terry, R. "Interrelations among the lesions of normal and abnormal aging of the brain", In: *Progress in Brain Research*, Swaab et al. (eds), Elsevier Science Publications, 1986, Vol. 70, pp. 41–7).

Long-term study of hippocampal tissue is possible by maintaining hippocampal slices on porous membranes at the air-medium interface. The long-term hippocampal slice prepared with this method exhibits long-term potentiation, a marker for relatively mature telencephalic connections. The slicesretain or develop many features characteristic of the mature hippocampus including elaborated dendritic spines and pathologic responsiveness, and remain stable for periods of weeks (Stoppini et al. A simple method for organotypic cultures of nervous tissues. J Neurosci Meth. (1991) 57:985–94.; reviewed in Bahr, B. A. Mini-review: Long-term hippocampal slices: a model system for investigating synaptic mechanisms and pathologic processes. J. Neurosci. Res (1995) 42:294–305). Treatment of this type of culture with chloroquine, a lysosomotropic agent, results in the appearance of carboxy-terminal fragments of the amyloid precursor protein (APP), an accumulation of β-amyloid immunoreactivity, and a loss of synaptophysin, a characteristic protein of the neural synapse, in the hippocampal slices. Pre-treatment with kainic acid made the build-up of β-amyloid-containing fragments and the loss of synaptophysin more rapid (Bahr, BA et al. Induction of β-amyloid-containing polypeptides in hippocampus: Evidence for a concomitant loss of synaptic proteins and interactions with an excitotoxin. Exp. Neurol. (1994) 129:81–94).

Other methods used to culture neuronal cells to study aging include (1) conventional in vitro methods used to study long-term plasticity which include rotation-mediated aggregating cell cultures (Chaterjee, S. and Nolder, M. "An aggregate brain cell culture model for studying neuronal degeneration and regeneration" J. Neural Transm. Suppl (1994) 44:47–60) or (2) slice cultures where the slices are incubated in sealed Maximov chambers (Crain, S. M. Neurophysiologic studies in tissue culture. (1976). New York. Raven Press) or (3) slice cultures where the slices are adhered to glass coverslips and rotated in medium-containing tubes for feeding (Gahwiler, B. H. Organotypic monolayer cultures of nervous tissue. J. Neurosci. Meth. (1981) 4:329–42; reviewed in Gahwiler, B. H. Organotypic cultures of neural tissue. Trends Neurosci. (1988) 11:4–84–9.).

SUMMARY OF THE INVENTION

An in vitro model of brain aging is provided by treating a brain tissue slice with compounds which interact with the brain and cause the development of characteristics of brain aging. The treatment compounds include: (1) a free radical generator, (2) agents that depress lysosomal enzymes, specifically inhibiting the cathepsins or preferably (3) a combination of (1) and (2). The treatment can be carried out before, after or simultaneous with the addition of a test compound, e.g., a drug. A variety of agents can be used as free radical generators including any metal salts (e.g., iron, cobalt, nickel, copper, manganese, vanadium), hydrogen peroxide, or a mixture of xanthine and xanthine oxidase. Cysteine lysosomal proteases such as cathepsin L, cathepsin B, cathepsin H, cathepsin S, cathepsin N, cathepsin T, carboxypeptidase B, and dipeptidase II are inhibited with agents such as N-CBZ-L-phenylalanyl-L-alanine diazomethylketone (ZPAD), or N-CBZ-L-phenylalanyl-L-phenylalanine diazomethylketone (ZPPD), or other diazomethyl ketones, leupeptin, chymostatin, CA-074 (methyl ester), cystatins, PLCPI (pig leukocyte cysteine proteinase inhibitor), E-64, or the calpain inhibitors I and II. This treatment has been found to induce several important features of aging (degradation of cytoskeletal proteins, increased numbers of perikaryal lysosomes, occasional pyknotic neuronal nuclei, increases in the level of cathepsin D mRNA, meganeurite formation, and abnormal fragmentation of APP), in long-term hippocampal slices. In a specific embodiment brain slices treated with cathepsin inhibitors such as (ZPAD) are additionally exposed to combinations of chemicals that provide free radicals, such as ascorbic acid and ferrous sulfate. This treatment results in the formation of neuronal auto-fluorescent granules that exhibit the features of lipofuscin granules. Accordingly, the in vitro model of the invention can be used to assay compounds for their utility in treating patients exhibiting symptoms of brain aging.

A primary object of the invention is to provide an in vitro assay method useful as a preliminary screen for compounds which reduce the symptoms, rate and/or physical effects of brain aging.

Another object is to provide a brain aging assay wherein lipofuscin granules appear in the cultured brain slices in a manner similar to the appearance in an aging brain (i.e., in the perikaryal cytoplasm of neurons and glia, in dendrites, and in meganeurites).

Another object is to provide a method for measuring aging of the cells of the brain (e.g., cells of the hippocampus) of a mammal, using an in vitro system.

Another object is to utilize the treatment of the organ cultures with (1) free radical generators (e.g., ascorbic acid and ferrous sulfate) or (2) lysosomal enzyme inhibitors (e.g., ZPAD), or a combination of (1) and (2) to develop drugs intended to prevent or reverse age-related pathologies.

Yet another object is to provide an in vitro model of disease, such as the condition known as neuronal ceroid lipofuscinosis (NCL).

Still another object is to utilize the in vitro model of NCL to identify potentially useful drugs for treating the condition.

One advantage of this system is it uses cultured telencephalic (e.g., hippocampal) slices, a system in which neurons mature in their normal association with other cells (e.g., neurons and glia), and maintain a variety of differentiated characteristics.

Another advantage is that the major features of the aging process are recapitulated in a short and experimentally manageable time frame.

Yet another advantage is the nature of the in vitro system, in that a large number of tissue slices can be run at the same time, allowing the effect of several drugs, or several dosages of a single drug, to be analyzed at the same time under controlled conditions.

A feature of this system is the ability to detect brain aging in an in vitro system by the production of neuronal autofluorescent granules that exhibit the features of lipofuscin granules, along with one or more other cardinal characteristics of the aged brain—particularly a human aged brain.

These and other objects, advantages and features of the invention will become apparent to those skilled in the art upon reading the following disclosure and description of the invention.

DESCRIPTION OF THE PREFERRED EMBODIMENTS

Before the present brain aging assays and methods of making and using such are described, it is to be understood that this invention is not limited to the particular assays, methods, free radical generators or enzyme inhibitor described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and," and "the" include plural referents unless the contexts clearly dictate otherwise. Thus, for example, reference to "a free radical generator" includes mixtures and large numbers of such, reference to "an oxidizing or reducing agent" includes large numbers of such compounds and mixtures thereof, and reference to "the assay method" includes one or more methods or steps of the type described herein.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated hereinby reference for the purpose of disclosing and describing specific aspects of the invention for which the publication is cited with connection with.

Definitions

The term "brain aging" is used to describe results observed with the normal biological progression of events occurring over time in a normal brain. Brain aging results in the production of a diverse set of biological features that include: (1) the generation of autofluorescent lipofuscin granules, (2) an increase in the level of cathepsin D mRNA, (3) an increase in the protein level of cathepsin D, (4) translocation of cathepsin,D protein from lysosomes to cytoplasm, (5) fragmentation of cytoskeletal proteins, (6) aberrant cleavage of APP, (7) an increase in the number of perikaryal lysosomes, (8) formation of lysosome-filled meganeurites, and (9) neurites containing fused dense bodies and vacuoles. Aging is further intended to mean the biological progression of events that occur during a disease process that affects the brain, which mimic or substantially mimic all or part of the aging events which occur in a normal brain, but which occur in the diseased state over a shorter period of time. Further, the term encompasses the progression of biological events within an in vitro assay system which biological events mimic or substantially mimic the aging process of a normal or diseased brain such as by mimicking one or more measurable characteristic(s) associated with normal brain aging.

The term "free radical generator" is intended to mean a single compound that generates free radicals, or a combination of compounds which together can generate a free radical. Specifically, a compound which generates (or combination of compounds which, when combined, generate), an atom or group of atoms or molecules which possess an odd (unpaired) electron. For example, hydrogen peroxide is a free radical generator as is nitric oxide. Further, a free radical generator is provided by combining a metal salt, such as ferrous sulfate, with a compound that can cause a redox cycle (an oxidizing or reducing agent, depending on the valance of the metal salt), such as ascorbic acid. Any redox reaction whereby a metal ion (e.g., iron,cobalt nickel) changes valences (e.g., Fe2+–>Fe3+) can be used to generate a free radical. It is also possible to generate free radicals by applying heat. The heating of organic peroxides (RO:OR) will result in the generation of RO• i.e., a free radical which can be cooled and applied to the brain slice at body temperature. Alternatively, free radical formation can be induced by (1) exposure to γ-irradiation, (2) exposure to UV illumination, (3) exposure to anoxia, (4) exposure to hypoxia (such as exposure to 25%–95% oxygen for minutes to weeks), or (5) supplementation of the culture media with superoxide radicals (such as by adding potassium superoxide to the culture media), (6) addition of cumene hydroperoxide, (7) addition of free radical generators such as paraquat, menadione, or napthazarine, (8) exposure to enzymatic reaction(s) (e.g., glucose and glucose oxidase; xanthine and xanthine oxidase; and hypoxanthine and xanthine oxidase), (9) exposure to an excitatory amino acid receptor agonists (e.g., NMDA, kainate, or glutamate), (10) exposure to the β-amyloid 1–42/43 fragment or the β-amyloid 25–35 fragment, (11) exposure to hydrogen peroxide, or (12) exposure to metal salts alone, if appropriate reducing or oxidizing agents are already present in the media or cell type used.

The term "brain slice" is intended to mean a planar piece of brain tissue preferably having a thickness of greater than 0.05 millimeter and less than 1 centimeter. The slice preferably includes brain tissue taken from any telencephalic brain region (e.g., the hippocampus, frontal cortex, or parietal cortex). The brain is preferably a mammalian brain and more preferably human.

The term "observed aging effect" is intended to mean the formation of granules which can be observed under a microscope. More specifically, per the present invention an observed aging effect includes general tissue autofluorescence which is seen at 10x magnification, while granule recognition can be made at magnifications greater that 25x, and preferably 100x. The lipofuscin autofluorescence occurs when tissue sections are irradiated by ultraviolet or blue light. Autofluorescent granule formation occurs in combination with other aging effects, which include an increase in the level of cathepsin D mRNA, and increase in the protein level of cathepsin D, translocation of cathepsin D protein from lysosomes to cytoplasm, fragmentation of cytoskeletal proteins, aberrant cleavage of APP, an increase in the number of perikaryal lysosomes, formation of lysosome-filled meganeurites, and neurites containing fused dense bodies and vacuoles, all of which can be measured or "observed" by procedures employed by those skilled in the art.

The term "lipofuscin" is defined as a substance which has certain histochemical characteristics, prominent among which is autofluorescence. Lipofuscin emits yellow-green/orange/red autofluorescence when irradiated by ultraviolet or blue light. Specifically, lipofuscin is excited by wavelengths of 275–450 nm and emits wavelengths of 450–650 nm. Lipofuscin granules appear as spherical puncta, ranging in size from 1–3 μm, within the cytoplasm of nerve cells. In electron micrographs, lipofuscin appears as electron dense, single-membraned compartments that contain various inclusions, such as membranous bands and vacuoles. The chemical makeup of the substance has recently been identified; lipofuscin granules are primarily composed of lipids and proteins, but additionally contain aluminum, copper, iron and dolichols. Lipopigment is considered to contain material resulting from cell damage (or disease) and from the normal process of cellular catabolism (Glees, P., and Hansan, M. Lipofuscin in neuronal aging and diseases", Normal Pathol. Anat. (1976) 32:1–68). The granules contain polymerized residues of peroxidized lipids and proteins incorporated into membrane-bound secondary lysosomes by autophagocytosis of cellular constituents (Harman, D. "Lipofuscin and ceroid formation: the cellular recycling system", in Porta, E. A., ed. *Lipofuscin and ceroid pigments*. New York: Plenum Press; 1990:3–15).

The terms "inhibitor" and "inhibitor of lysosomal enzyme" and the like are used interchangeably herein to describe compounds which inhibit the lysosomal enzymes (specifically proteases), either directly or indirectly. Examples of the cysteine lysosomal proteases include cathepsin L, cathepsin B, cathepsin H, cathepsin S, cathepsin N, cathepsin T, cathepsin C, carboxypeptidase B, and dipeptidase II. A direct inhibitor acts on the protease itself; examples of suitable direct inhibitors include ZPAD, ZPPD, other diazomethyl ketones (e.g. Z-Phe-Tyr(tBu)-diazomethylketone, Z-Val-Val-Nle-diazomethylketone, or Z-Phe-Lys-2,4,6-trimethyl-benzoyloxy-methylketone HCl), chymostatin, CA-074 (methyl ester), cystatins, PLCPI (pig leukocyte cysteine proteinase inhibitor), leupeptin, E-64, and calpain inhibitors I and II. Indirect inhibitors of the lysosomal proteases are compounds which act by elevating the intra-lysosomal pH; examples of suitable indirect inhibitors include chloroquine, ammonia, and bafilomycin A.

The term "ZAPD" refers to N-CBZ-L-phenylalanyl-L-alanine-diazomethyl ketone which is a specific inhibitor of lysosomal enzyme or more specifically an inhibitor of lysosomal protease such as cysteine lysosomal protease, still more specifically an inhibitor of cathepsin B and cathepsin L—see Bednarski, et al., J. Neurochem. 67, 1846–1855 (1966) incorporated herein by reference in its entirety. These and other lysosomal enzymes as inhibited by other inhibitors such as ZPPD which refers to N-CBZ-L-phenylalanyl-L-phenylalanine diazomethylketone and other diazomethyl ketones.

General Aspects

Cultured brain slices are treated in a manner which causes the brain slice to develop characteristics of brain aging. The treatment can be with any of (1) one or more free radical generators or (2) one or more lysosomal enzyme inhibitors or (3) preferably a combination of (1) and (2). The treated brain slices rapidly develop autofluorescent lipofuscin granules—a universal feature of brain aging. Other correlates of the aged brain also developed thereby providing an in vitro model for (1) the study of brain aging; (2) assessment of anti-brain aging drugs; and (3) therapeutics directed at the clinical condition referred to as NCL.

One of the important features of the present invention is to use the brain slices which can be induced to develop characteristics of aging to test the effects of drugs on the brain. The brain slice can be treated to induce the effects of aging followed by the addition of drug to be tested. Per this sequence of events the drug is tested to determine its ability to reverse the effects of aging which have been induced in the brain slice. In another scenario the drug can be added at the same time that brain aging is induced. In this scenario the drug is being tested as a prophylactic, i.e., can it prevent the development of brain aging effects? Lastly, the drug can be added to the brain slice after the effects of aging are induced. In this scenario if the drug attenuates the development of the characteristics of brain aging it could be used for its maintenance effects. In each scenario it is preferred to carry out the assay with one or perhaps three control groups. The first control group could be brain slices wherein the development of brain aging effects were induced per the present invention but no drug is added. The second control group could be the brain slices with drug added without having the development of aging effects induced per the present invention. A third control group could also be used wherein the brain slices were not treated in any manner but were maintained in a normal brain slice culturing environment. The fourth group is the experimental group with aging induced per the invention and test drug added before, during and/or after inducement.

The invention circumvents problems that have hindered past research in neurogerontology in two specific ways. First, it uses cultured telencephalic brain regions. Specifically, in hippocampal slices, the neurons mature in their "normal" associations with other cells (neurons and glial) and stably maintain a variety of adult characteristics. Alternatively, slices from other telencephalic regions, such as the neocortex, can be used. The above described features relating to brain aging distinguish the treated cultured slices described here from other forms of tissue culture, and provide cytoarchitecture and connectivity quite similar to that observed in vivo. Secondly, when the slices of brain tissue are treated as described herein, they exhibit a salient characteristic of normal brain aging—they exhibit the accumulation of autofluorescent "lipofuscin" granules within neuronal perikarya and proximal processes.

Lipofuscin granules begin to appear in the brain in early adulthood and then increase dramatically as aging progresses. The granules have been found in all mammals so far examined, and occur in a broad collection of brain regions including the neocortex. Accordingly, lipofuscin accumulation has been shown to be a distinctive characteristic of brain aging. Thus, any brain aging model which did not reproduce lipofuscin accumulation would be very incomplete. The accumulation of lipofuscin granules is associated with normal aging (Mann, D. M. A. et al., "The relationship between lipofuscin pigment and ageing in the human nervous system", (1978) J. Neurol. Sci. 37:83–93; Braak, H. "Spindle-shaped appendages of IIIab-pyramids filled with lipofuscin: A striking pathological change of the senescent human isocortex", (1979) Acta Neuropathol. 46:197–202.). As the brain ages, lipofuscin accumulates at different rates in different types of neurons, although there is evidence that cell size and past functional activity influence lipofuscin deposition (Finch, C. E., (1990) *Longevity, sensescence, and the genome*, University of Chicago Press, Chicago). Moreover, there is also evidence to suggest that an increased rate of lipopigment formation related to membrane and lysosomal abnormalities occurs in Alzheimer's disease (Dowson, J. H. et al. "Changes in intraneuronal lipopigment in Alzheimer's disease", (1992) Neurobiol. Aging 13:493–500).

In some individuals, lipofuscin builds up at an abnormally rapid pace, resulting in brain cells that appear to be aged well beyond what would be expected from the subjects' chronological age. This condition is referred to as NCL and is accompanied by a variety of deleterious symptoms. Brain slices treated with free radical generators in the presence or absence of inhibitors of lysosomal proteases may serve to provide an in vitro model for this disease process.

Lipofuscin granule formation is a universal feature of brain aging. The percentage of neurons which contain lipofuscin in a sample can be determined using light microscopic techniques, and the lipofuscin content of an individual neuron can be assessed by determining the area of the lipopigment-containing region (Dowson, J. H. et al. "changes in intraneural lipopigment in Alzheimer's disease", (1992) Neurobiol. Aging 13:493–100.) Alternatively, the fluorescence of lipofuscin can be quantitated in a tissue sample using a lipid extraction procedure combined with spectrofluorimeter analyses (Tappel, A. et al., "Effect of Antioxidants and Nutrients on Lipid Peroxidation Fluorescent Products and Aging Parameters in the Mouse," J. Gerontol. (1973) 28(4):415–24.)

Accordingly, efforts to develop an in vitro model of brain aging included attempts to induce the build-up of lipofuscin bodies in cultured slices. Initial efforts involved using various treatments that disrupt lysosomal functioning. Over time, it was determined that depressing two lysosomal proteases, cathepsin B and cathepsin L, induced several important features of the aged brain as well as certain age-related neuropathologies. Because initial efforts to induce lipofuscin with this approach were unsuccessful, it was not possible to develop a model of normal brain aging. In the absence of the cardinal signs of aging, it would be difficult to argue that the pathologies elicited by lysosomal perturbations alone in cultured slices grew out of the kinds of age-related processes that actually occur in vivo.

Because earlier attempts did not generate lipofuscin, a new approach was taken which involved (1) acute exposure to any chemicals that generate free radicals or (2) chronic treatment. with the inhibitors of the two cathepsins or (3) a combination of (1) and (2). The first (1) and third (3) procedures unambiguously induce lipofuscin granule formation in a cultured brain slice—thus the cultured brain slices exhibit the universal sign of brain aging. The present procedure provides a means for investigating the causes of NCL and possible ways of treating it.

Treating brain slices as described herein will result in the slices developing major features of the aging process within a short and experimentally manageable time frame. Measurement of the age-related changes in cultured slices is straightforward. Further, the system is much more accessible to experimental manipulations than in vivo preparations. Because large numbers of slices can be run at the same time, it is possible to test several drugs or dosages in a single experiment. Simultaneous testing of multiple drugs or dosages is not realistic in neurogerontological work on animals. Thus, the invention, exhibiting as it does essential characteristics of the aged brain, is a unique platform for developing drugs intended to prevent or reverse the development of age-related pathologies.

Specific Assay Information

General characteristics of the assay of the invention were described in the above "General Aspects" section in order to provide an overview of how the brain assay and methodology of the present invention can be carried out. Those skilled in the art will contemplate various modifications of the methodology based on that general disclosure. In order to provide a more specific disclosure the following detailed information can be used in order to generate brain cultures of the invention in which brain cultures will develop lipofuscin granules.

1. Lysosomal enzyme inhibitor is added to culture media and exposed to brain tissue at a concentration of 0.1–50 $\mu$M. This approximates 1.0–18 $\mu$g of inhibitor per approximately 200 $\mu$g of brain tissue. Inhibitor can be added alone or with a combination of (2) and (3) below.

2. Ascorbic acid is added to culture media and exposed to brain tissue at a concentration of 7.0–12.0 mM. This approximates 1.0–4.0 mg of ascorbic acid per approximately 200 $\mu$g of brain tissue. The ascorbic acid is added in combination with (3) below to generate free radicals i.e., combined with any metal salt which will generate free radicals.

3. Ferrous sulfate is added to culture media and exposed to brain tissue at a concentration of 0.3–3.0 mM. This approximates 0.1–0.8 mg of ferrous sulfate per approximately 200 $\mu$g of brain tissue. The ferrous sulfate or other salt is added with ascorbic acid or other reducing agent to form a free radical. The free radical generators can be added alone or with the inhibitor of (1) above.

4. At high doses of inhibitor (45 $\mu$M; 18 $\mu$g/200 $\mu$g tissue) some aging effects are exhibited as soon as one day. Treatment is generally carried out over a period of at least three days 5. Ascorbic acid/ferrous sulfate exposure is done for 20–60 minutes. Treated brain tissue is then examined in about one to five days. Some lipofuscin granules can be seen after 12 hours after a 20 minute exposure to the agents. However, it is preferable to wait at least 24 hours.

6. Free radical generators alone can produce the autofluorescence. ZPAD is used to produce additional characteristics (i.e., lysosomal hyperplasia, cathepsin D in the cytosol, meganeurite formation) of brain aging.

The slice culture system described has demonstrated that neurons develop features that characterize normal brain aging. Specifically brain aging is shown by subjecting cultured brain slices to the combined exposure of (1) compounds that suppress the activities of two lysosomal enzymes and/or (2) agents that generate free radicals. To obtain inhibition of lysosomal enzymes, the majority of the experiments used N-CBZ-L-phenylalanyl-L-alanine-diazomethylketone (ZPAD), an inhibitor of cathepsin B and cathepsin L. Experiments using more selective inhibitors of cathepsin L (i.e., N-CBZ-L-phenylalanyl-L-phenylalanine-diazomethylketone and chymostatin) have replicated several of the ZPAD-induced alterations. Based on the results obtained, it would be reasonable to expect that other compounds that significantly suppress the activity of cathepsin L would likely result in the generation of similar age-associated features.

The ZPAD-treated slices were briefly exposed to ascorbic acid and an iron salt (ferrous sulfate), a mixture known to generate reactive oxygen species.

The following characteristics of the aged brain were observed in cultured slices exposed to ZPAD for 3–6 days:
  a. degradation of three cytoskeletal proteins;
  b. increased concentrations of cathepsin D in lysosomes and in the cytoplasmic compartment;
  c. increased numbers of perikaryal lysosomes;
  d. occasional pyknotic (i.e. seemingly dying) neuronal nuclei.
  e. fusiform expansions or "meganeurites" extending off neuronal cell bodies.

Hippocampal slices maintained in culture for 7 additional days after the conclusion of ZPAD treatment exhibited some additional features not found in slices removed immediately after a six day treatment with the drug. These characteristics included:
  f. Increased numbers of cells containing meganeurites
  g. Meganeurites containing circular compactions of dense lysosomes and vacuoles.
  h. groups of neuronal profiles containing fused lysosomes and vacuoles in close association with astrocytes.

Treatments of cultured brain slices with a combination of ZPAD and free radical-generating compounds (i.e., ferrous sulfate and ascorbic acid) led to the additional production of neuronal autofluorescent granules that exhibit the key features (i.e., appearance, excitation wavelength, color when viewed under ultraviolet illumination) typically used to identify lipofuscin pigments in aged brain tissue.

Uses

The present invention provides an in vitro model for brain aging which is produced by treatment with (1) a free radical generator, (2) agents which depress lysosomal enzymes, or preferably (3) a combination of (1) and (2).

The characteristic features of brain aging can be produced by any compound at any concentration that causes the desired effect. In the other embodiments, the following free radical generators can be used in the assay at the concentrations listed in Table 1.

TABLE 1

| Compound | Concentration Normally Used | Range of Concentrations That May Result in Similar Effects |
| --- | --- | --- |
| Metal Salt + Redox Agent | (1 mM) + (10 mM) | (0.05–20 mM) + (0.1 mM–100 mM) |
| Hydrogen Peroxide | 100 $\mu$M | 5 $\mu$M–300 mM |
| Cumene Hydroperoxide | 50 $\mu$M | 1 $\mu$M–5 mM |

TABLE 1-continued

| Compound | Concentration Normally Used | Range of Concentrations That May Result in Similar Effects |
| --- | --- | --- |
| Naphthazarine | 5 μM | 0.1 μM–150 μM |
| Paraquat | 1 mM | 10 μM–30 mM |
| Menadione | 50 μM | 1 μM–500 μM |
| Xanthine + Xanthine Oxidase | (100 μM) + (10 mu/ml) | (1 μM–500 μM) + (0.5–200 mu/ml) |
| Glucose Oxidase (assume glucose is already present in media) | 7.5 mu/ml | 0.5–200 mu/ml |

Use of the above listed compounds at the lower limit or above will provide the desired results. Thus the inclusion of an upper limit is not a limitation on the scope of the invention. Use of the listed compounds in amounts above the upper limits listed (although unnecessary) will still provide results.

The range of concentrations used is wide enough to allow for significant differences in exposure duration. For example, effects that can be induced by a brief exposure to hydrogen peroxide (100 mM for 10 minutes) may be comparable to those caused by longer exposure to lower levels of the compound (10 μM for 2 days).

In the other embodiments, the following lysosomal inhibitors can be used in the assay at the concentrations listed on Table 2.

TABLE 2

| Compound | Concentration Normally Used | Range of Concentrations That May Result in Similar Effects |
| --- | --- | --- |
| ZPAD | 40 μM | 0.05 μM–300 μM |
| ZPPD | 10 μM | 0.05 μM–300 μM |
| E-64 | 30 μM | 1 μM–300 μM |
| Leupeptin | 50 μM | 1 μM–300 μM |
| Nα-t-Boc-deacetylleupeptin | 50 μM | 1 μM–300 μM |
| Calpain Inhibitor I | 150 μM | 1 μM–300 μM |
| Calpain Inhibitor II | 150 μM | 1 μM–300 μM |
| Chloroquine | 60 μM | 1 μM–150 μM |
| Bafilomycin A | 0.5 μM | 0.01 μM–10 μM |
| Chymostatin | 2.5 μM | 0.05 μM–300 μM |
| PLCPI | 0.5 μM | 0.01 μm–300 μM |
| CA-074 (methyl ester) | 1.0 μM | 0.01 μM–300 μM |
| Cystatin A | 0.5 μM | 0.01 μM–300 μM |

Use of the above listed compounds at the lower limit or above will provide the desired results. Thus the inclusion of an upper limit is not a limitation on the scope of the invention. Use of the listed compounds in amounts above the upper limits listed (although unnecessary) will still provide results.

The assay is designed to test drugs for their ability to prevent, reverse or stabilize brain aging and to study diseases, such as NCL, which mimic the rapidly aging brain. In addition, the culture method can be used to study any other diseases which exhibit the effects of the rapidly aging brain. The invention can also be used to study the following disorders:

1. Alzheimer's Disease
2. Down's Syndrome
3. Lysosomal storage diseases
   a. Niemann Pick disease type C
   b. Classic Tay-Sachs disease (infantile $G_{M2}$-gangliosidosis, B-variant)
   c. Juvenile $G_{M2}$-gangliosidosis
   d. $G_{M2}$-gangliosidosis, AB variant
   e. Hurler's disease
4. Lewy body disease
5. Progressive supranuclear palsy

EXAMPLES

The following examples are put forth so as to provide those of ordinary skill in the art with a complete disclosure and description of how to make a brain aging assay and carry out the methodology for using such assays, and are not intended to limit the scope of what is regarded as the invention. Efforts have been made to insure accuracy with respect to numbers used (e.g., amounts, temperature, etc.) but some experimental errors and deviations should be accounted for. Unless indicated otherwise, parts or parts by weight, molecular weight is weight average molecular weight; temperature is in degrees centigrade; and pressure is at or near atmospheric.

Example 1

Hippocampal slices were prepared from 10–13 day-old Sprague-Dawley rats and maintained in culture using the method of Stoppini et al. (1991, supra). Briefly, the hippocampi were dissected in ice-cold artificial cerebrospinal fluid (124 mM NaCl, 10 mM glucose, 3 mM KCl, 1.25 mM $KH_2PO_4$, 4 mM $MgSO_4$, 2 mM $CaCl_2$, 26 mM $NaHCO_3$, 2 mM ascorbate, 0.1 mM ascorbate, pH=7.3), and 400 μm thick slices were produced on a McIlwain tissue chopper. One ml of culture media (50% Basal Medium Eagle, 25% Earle's Balance Salt Solution, 25% horse serum), supplemented with 136 mM NaCl, 2 mM $CaCl_2$, 2.5 mM $MgSO_4$, 5 mM $NaHCO_3$ 3 mM glutamine, 40 mM glucose, 0.5 mM ascorbic acid, 20 mM HEPES (pH=7.3), 1 mg/L insulin, 5 U/ml penicillin and 5 mg/L streptomycin, was added to each well of a six well culture plate, and inserts containing a polystyrene membrane (pore size: 0.4 μM) were placed in each well to support the hippocampal sections. Slices were incubated in a humidified, 37° C. atmosphere containing 5% $CO_2$ and maintained in culture for at least nine days before experiments were initiated. Media was replenished on the first day after explantation, and every 2–3 days during the initial culture period. A subset of the hippocampal slices in the six-well culture dishes was exposed to media (as described above, with heat-treated horse serum) containing 30–50 μM ZPAD (BACHEM Bioscience, Inc., Torrance, Calif.). Tissue was harvested after three to six days of continuous ZPAD exposure.

Western blot analyses of slices exposed to ZPAD revealed a 3-fold increase in the protein level of cathepsin D ($p<0.001$, Mann-Whitney, 2 tails, n=8) and the proteolytic degradation of four cytoskeletal proteins (tubulin, spectrin, and microtubule-associated protein-2). The fragmentation of intact tau proteins resulted in particularly stable 29 kDa species ($tau_{29}$) that were accessible to cytosolic protein kinases. Moreover, Western blots of subcellular fractions indicated that ZPAD-exposed slices exhibited markedly elevated levels of active cathepsin D protein in both lysosomal and non-lysosomal (cytosolic) compartments. In addition, Western blots revealed increased levels of 25–30 kDa fragments of amyloid precursor protein in slices treated with 45 μM ZPAD for six days.

In order to determine if ZPAD treatment changed the expression of cathepsin D, in situ hybridization analyses were performed. These studies revealed that after four days of exposure to 45 μM ZPAD, CA3 neurons exhibited a 56% increase in the level of cathepsin D mRNA, and glial cells of subfield CA1 stratum radiatum exhibited a 71% increase in the level of cathepsin D mRNA (p<0.01, t-test, 2 tails).

Further experiments using the electron microscope revealed that slices treated with 45 μM ZPAD for six days had a dramatic increase in the number of lysosomes in the perikarya of neurons and glia throughout the tissue. Furthermore, lysosomes in CA1 and CA3 pyramidal cells were not restricted to the soma but instead were located throughout dendritic processes. Clusters of lysosomes were commonly found within bulging segments of proximal dendrites that were notable for an absence of nicrotubules and neurofilaments. The cell bodies of a small percentage of CA1 neurons were cleared of the excess lysosomes but had gained fusiform, somatic expansions that were filled with lysosomes and related complex, dense bodies. These appendages are similar in form and content to structures previously referred to as "meganeurites." While pyknotic nuclei were sometimes encountered, most of the cells in slices exposed to ZPAD for six days appeared relatively normal. These results are in contrast to features noted in hippocampal slices treated with ZPAD for six days and then maintained in culture for seven additional days without ZPAD. In these slices, meganeurite-containing CA1 pyramidal cells were more commonly found. The distal portions of long meganeurites contained large numbers of electron-dense lysosomes and vacuoles that were compacted into circular aggregates. Aggregates of this type were also found within membrane-bound cellular processes (neurites) flanking the pyramidal cell layer. Astrocytes were commonly located in close proximity to groups of lysosome-laden neurites. It is noteworthy that meganeurites were not found on CA3 neurons or granule cells.

Example 2

Hippocampal slices were prepared and placed into culture as described above. A subset of the hippocampal slices in the six well culture dishes were exposed to media containing 30–50 μM ZPAD. After six days in culture, in the presence or absence of ZPAD, a subset of the hippocampal slices were then treated with 10 mM ascorbic acid and 1 mM ferrous sulfate in culture media. After a 20–30 minute exposure, the free radical generators were removed, and fresh culture media was added. Slices were fixed one and two days after the free radical insult and processed for light microscopy in order to determine tissue autofluorescence.

In the cultures treated with free radical generators, light microscopic examination revealed the accumulation of autofluorescent granules within the cytoplasm of neurons. The form of the granules and gexcitation/emission properties of the fluorophore were notably similar to lipofuscin. Approximately 30–50% of neurons exhibited autofluorescent granules one day after the treatment with the free radical generators, while 50–70% of the neurons exhibited lipofuscin two days post free radical treatment. It should be noted that neurons from control slices, which were not exposed to the free radical generators, did not exhibit appreciable levels of autofluorescent granules.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. An in vitro assay method for identifying an agent that reduces a symptom associated with brain aging, said method comprising:
   (a) contacting a brain tissue in vitro with: (i) an inducing agent that induces an increase in the number of lysosomes in said brain tissue, wherein an increase in the number of lysosomes is a symptom of brain aging; and (ii) a test agent, to produce a test brain tissue; and
   (b) determining the effect of said test agent on the increase in the number of lysosomcs in said test brain tissue, compared with a control brain tissue not contacted with said test agent, wherein a reduction the number of lysosomes in said test brain tissue compared to the number of lysosomes in said contld brain tissue indicates that the test agent reduces a symptom associated with brain aging.

2. The method of claim 1, wherein said brain tissue is a brain slice.

3. The method of claim 2, wherein the brain slice is selected from the group consisting of a hippocampal slice, an entorhinal cortex slice, an entorhinohippocampal slice, a neocortex slice, a hypothlalamic slice, and a cortex slice.

4. The method of claim 1, wherein said inducing agent comprises a free radical generator.

5. The method of claim 1, wherein said inducing agent comprises an inhibitor of a lysosomal enzyme.

6. The method of claim 5, wherein Lhe inhibitor is N-CBZ-L-phenylalatiyl-L-alanine diazomethylketone or N-CBZ-L-phenylalanyl-L-phenylalanine-diazomethylketone.

7. The method of claim 1, wherein said inducing agent comprises a free radical generator and an inhibitor of lysosomal enzyme.

8. The method of claim 1, wherein the test agent is applied to the brain tissue prior to said inducing agent.

9. The method of claim 1, wherein the test agent is applied to the brain tissue after said inducing agent.

10. An in vitro assay method for identifying an agent that reduces a symptom associated with brain aging, said method comprising:
    (a) contacting a brain tissue in vitro with: (i) an inducing agent that induces formation of megancurites in said brain tissue, wherein formation of meganeaurites is a symptom of brain aging; and (ii) a test agent, to produce a test brain tissue; and
    (b) determining the effect of said test agent on the production of meganeurites in said test brain tissue, compared with a control brain tissue not contacted with said test agent, wherein a reduction in the number of meganeyrutes in said test brain tissue compared to the number of meganeurites in said control brain tissue indicates that the test agent reduces a symptom associated with brain aging.

11. The method of claim 10, wherein said brain tissue is a brain slice.

12. The method of claim 11, wherein the brain slice is selected from the group consisting of a hippocampal slice, an entorhinal cortex slice, an entorhinohinohippocampal slice, a neocortex slice, hypothalamic slice, and a cortex slice.

13. The method of claim 10, wherein said inducing agent comprises an inhibitor of a lysosomal enzyme.

14. The method of claim 13, wherein the inhibitor is N-CBZ-L-phenylalanyl-L-alanine diazomethylketone or N-CBZ-L-phenylalanyl-L-phenylalanine-diazomethylketone.

15. The method of claim 10, wherein the test agent is applied to the brain tissue prior to said inducing agent.

16. The method of claim 10, wherein the test agent is applied to the brain tissue after said inducing agent.

* * * * *